United States Patent [19]

Bokros

[11] 4,166,292
[45] Sep. 4, 1979

[54] STRESS REINFORCED ARTIFICIAL JOINT PROSTHESES

[75] Inventor: Jack C. Bokros, Alpine, Calif.

[73] Assignee: Carbomedics, Inc., San Diego, Calif.

[21] Appl. No.: 831,488

[22] Filed: Sep. 8, 1977

[51] Int. Cl.² .............................................. A61F 1/24
[52] U.S. Cl. ...................................... 3/1.91; 3/1.911; 3/1.912; 128/92 C
[58] Field of Search ................................. 3/1.9–1.913, 3/1; 128/92 C, 92 CA

[56] References Cited

U.S. PATENT DOCUMENTS

| | | | |
|---|---|---|---|
| 3,698,017 | 10/1972 | Scales et al. | 3/1.912 |
| 3,707,006 | 12/1972 | Bokros et al. | 128/92 CA X |
| 3,728,742 | 4/1973 | Averill et al. | 3/1.911 |
| 3,852,830 | 12/1974 | Marmor | 3/1.911 |
| 3,869,731 | 3/1975 | Waugh et al. | 3/1.911 |
| 4,021,864 | 5/1977 | Waugh | 3/1.91 |
| 4,055,862 | 11/1977 | Farling | 3/1.91 |

*Primary Examiner*—Ronald L. Frinks
*Attorney, Agent, or Firm*—Fitch, Even & Tabin

[57] ABSTRACT

Artificial joint prostheses comprising an artificial graphite substrate of predetermined orthopedic shape, a pyrolytic carbon coating on said substrate, and a metallic band circumferentially compressively engaged with the exterior surface of said carbon coated substrate in a plane generally orthogonal to the loading axis and adjacent the articulating contact surface of the prosthesis.

5 Claims, 6 Drawing Figures

STRESS REINFORCED ARTIFICIAL JOINT PROSTHESES

The present invention relates to prosthetic devices, and more particularly, is directed to artificial joint prostheses utilizing a graphite substrate and a pyrolytic carbon coating.

The use of prosthetic devices for repair or replacement of bone structure in a living body is well known. Conventional prosthetic devices have been constructed from metals, ceramics, and plastics, depending upon the intended application. Many conventional artificial prostheses for artificial joint reconstruction, such as knee joint prostheses like that of U.S. Pat. No. 3,869,731, consist of a metallic articulating joint element, and a mating, ultra-high molecular weight polyethylene articulating joint element. A principal problem of these prostheses is caused by wear and/or cold-flow (creep) of the high molecular weight polyethylene component upon prolonged usage at the local levels which exist in the skeletal system.

Metallic joint components have a high modulus of elasticity and do not flex in harmony with the bone in which they are implanted; instead, they concentrate stress in portions of the remaining, lower modulus bone, particularly at the metal-bone interface.

As described in U.S. Pat. No. 3,707,006, joint prostheses comprising a dense graphite substrate with a pyrolytic carbon coating may be provided which have a modulus of elasticity approximating that of natural bone, and as further disclosed in copending application Ser. No. 766,024 entitled "Socket and Joint Prostheses" of Akins and Slivenko, improved sockets for ball joint prostheses may be provided in carbon joint elements. However, further improvements in carbon coated graphite prostheses, particularly in respect of minimizing tensile stresses in such prostheses, would be desirable.

Accordingly, it is an object of the present invention to provide improved joint prostheses. It is a further object to provide joint prostheses elements which have increased resistance to tensile stress resulting from skeletal load forces. These and other objects of the invention will be readily apparent from the following detailed description and the accompanying drawings of which:

Figure 1:
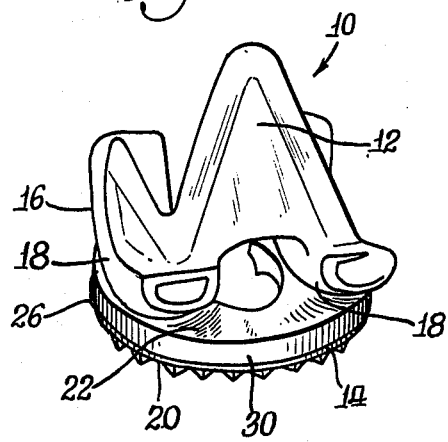
FIG. 1 is a perspective anterior view of an artificial knee prostheses having a compression ring reinforced tibial component.

Generally, the present invention is directed to functional artificial joint prosthesis elements for prolonged or permanent implantation in a living body.

The joint prosthesis elements of the present invention generally comprise an artificial graphite substrate having a predetermined shape adapted for articulating function, and having a modulus of elasticity in the range of that of natural living bone. A particularly preferred form of graphite for use as a substrate material is polycrystalline graphite, and an example of such a graphite is the polycrystalline graphite sold under the trade name POCO-AXF graphite having density of about 1.9 gm/cm, an average crystalline size of about 300 Angstroms, an isotropy of nearly 1.0 on the Bacon scale (BAF), and a modulus of elasticity of about $1.7 \times 10^6$ psi.

The substrate will also generally be suitably shaped for appropriate skeletal attachment, and is provided with a dense, isotropic pyrolytic carbon coating on the graphite substrate. The joint prosthesis elements of the present invention further comprise a high modulus metallic band in compressively loaded relationship with the perimeter of carboncoated joint element adjacent its articulating joint surface and in a plane generally perpendicular to the loading axis of the joint element.

As indicated, the substrate is generally provided in a predetermined, articulating joint functional shape, and is provided with a coating of pyrolytic carbon. The pyrolytic carbon coating may be applied to the substrate in a suitable manner such as described in U.S. Pat. No. 3,707,006, the disclosure of which is hereby incorporated by reference. Preferably, the carbon coating is deposited through the use of an apparatus which maintains a substrate in motion while a coating process is carried out, to assure that the coating is uniformly distributed on the desired surfaces of the substrate. A rotating drum coater or a vibrating table coater may be employed for larger joint prostheses substrates. When the substrates are small enough to be levitated in an upwardly flowing gas stream, a fluidized bed coater is preferably used. For larger substrates, the supporting of a substrate on a rotating or stationary mandrel within a large fluidized bed may also be utilized.

Generally, when pyrolytic carbon is deposited directly on the surface of the substrate material, the conditions are controlled so that the pyrolytic carbon which is deposited has a coefficient of expansion of within plus or minus 25% of the coefficient of expansion of the substrate material, and preferably to within about plus or minus 20%. Because pyrolytic carbon has greater strength when placed in compression than when placed in tension, the thermal coefficient of expansion of the pyrolytic carbon is most preferably about equal to or less that that of the substrate. Under these conditions, good adherence to the substrate is established and maintained during the life of the prosthetic devices, and upon cooling of the pyrolytic coating - substrate composite, the pyrolytic carbon coating is placed in compression under conditions of its intended used at about ambient temperature.

As described in previously mentioned patents, the coatings may be substantially entirely pyrolytic carbon or may contain a carbide-forming additive such as silicon, which may be utilized to enhance or modify the overall mechanical properties of the coating. The pyrolytic carbon is considered to be particularly advantageous for constituting the surface of the joint prostheses because of its inertness and wear resistance properties.

The pyrolytic carbon surface of the prosthetic device may be fabricated with different physical properties at different surface locations. For example, a dense, polished wear surface is utilized at the articulating surface of the joint prostheses. A surface having a rough, or porous surface property may be employed at the surfaces at which the prostheses is to be joined with natural bone, to facilitate the development of a strong bone-prosthesis union. In addition to mechanical modification of the pyrolytic carbon surface such as by polishing, it may be desirable to utilize various other physical or chemical modifications of the pyrolytic carbon surface.

An important feature of the joint prostheses of the present invention comprises means for circumferentially compressing the joint element adjacent the articulating joint surface of the joint. In this connection, the application of compressional forces at the articulating joint interface produces transverse tensile strain in the joint element. This tensile strain may be localized in joint prostheses having complex, curved interacting surfaces. Such localized tensile strain is undesirable in the prostheses because of the inherent lack of tensile resilience of the carbonacious materials relative to various other materials, and the resulting material design requirements which may impede maximum functional design optimization for prosthetic purposes. In accordance with the present invention, transverse tensile strain is compensated by a relatively high modulus, compression-loaded metallic ring adjacent the articulating surface which reinforces the prosthesis against transverse localized tensile strain.

Turning now to the drawings, the present invention will now be further described with reference to the particular embodiments illustrated in the figures.

Illustrated in FIG. 1 is an artificial knee prostheses 10 for reconstructive knee joint repair. The knee joint prostheses comprises a femoral component 12 and a tibial component 14.

The femoral component 12 is adapted for implantation at the distal end of the suitably surgically prepared femur, and has two automatically shaped bearing surfaces 16, 18 to provide for normal knee motion. To accommodate anatomical motion, the bearing surfaces 16, 18 of the femoral component are defined by a continuous series of curves of diminishing radii, extending from the anterior portion to the posterior portion of the bearing surface. The femoral component is fabricated in one piece from isotropic polycrystalline graphite sold under the name POCO AXF graphite having a density of 1.9 g/cc and a modulus of $1.7 \times 10^6$ psi. The graphite substrate is provided with a dense isotropic pyrolytic carbon coating as described in U.S. Pat. No. 3,707,006. The pyrolytic carbon bearing surfaces 16, 18 are highly polished to provide a low friction and wear resistant surface for engagement with the tibial component 14.

The tibial component 14 is adapted to be affixed at its lower surface 20 to a suitably surgically prepared tibial plateau. The upper surface 22 mates in functional joint relationship with the bearing surfaces 16, 18 of the femoral component 12. The tibial component 12 can be U-shaped in axial view, with a central cavity 25, and is generally disc-shaped in side view, with a circumferential perimeter surface 26 which is generally parallel to the loading axis.

The undersurface 20 of the tibial component 12 is formed with a plurality of triangular cross-section ridges 24 to enhance permanent affixation of the prosthetic element of the tibia. The upper surface 22 of the tibial component is concave in respect of its intersection with the perimeter surface 26, for interaction with the convex bearing surfaces 16, 18 of the femoral component 12.

Like the femoral component, the tibial component is fabricated from a dense, isotropic polycrystalline POCO AXF-5Q graphite substrate having a density of 1.9 grams/cm³, and an elastic modulus of $1.7 \times 10^6$ psi. The shaped substrate is provided with a pyrolytic carbon coating as described in U.S. Pat. No. 3,707,006. The concave upper bearing surface 22 of the tibial component is highly polished for low friction and wear resistant contact with the mating femoral component surfaces. The perimeter surface 26 is also highly polished to accommodate a circumferential stress ring 30, for reasons which will now be more fully discussed.

In this connection, it will be appreciated that substantial axial compressive loads may be applied through the joint prosthesis by normal body motions. These compressive loads produce transverse tensile stresses, which are undesirable in the pyrolytic-carbon-coated substrate.

In order to counteract the tensile stresses, resulting from vertical loads transmitted from the femoral component, a metallic yoke or band 30 is provided for the tibial component 14 about the perimeter surface 26 adjacent the concave upper surface 22 of the component, and in a plane perpendicular to the vertical loading axis. The metal band 30 is provided in closely conforming compressional relationship against the polished exterior surface of the tibial component 14, and has a modulus of elasticity at least about five times and preferably at least ten times greater than that of the pyrolytic carbon-coated graphite substrate. The combination of the compressional relationship of the band with the carbon-coated substrate and the substantially larger modulus of the metallic band, reduces vertical-load-induced tensile strain in the carbon so that the resulting tensile load is primarily carried by the metallic band 30. The metal band does not carry any substantial portion of the axial compressive load transmitted through the tibial component from the femoral component to the tibia.

The optimum thickness of the metal band may vary depending on the particular application; in the illustrated embodiment of FIG. 1, the thickness of the band 30 is in the range of from about 1/16 of an inch to about ⅛ of an inch.

As indicated, the band 30 of the illustrated embodiment is in conforming, compressional relationship to the perimeter surface 26 of the implant 12. In this connection, the band may be pressed about the tibial component or may be shrunk to the tibial component by utilizing the thermal expansion properties of the metal band. Generally, only very small compressive forces in the unloaded state need be provided by such press-fit or shrink-fit procedures; because of the higher modulus of the band 30 with respect to the graphite substrate, the load forces will be preferentially transferred to the band 30.

In any event, the compressive loads of the band 30 should generally best not exceed any strain greater than about 0.3% at the perimeter surface 26.

Figure 2:
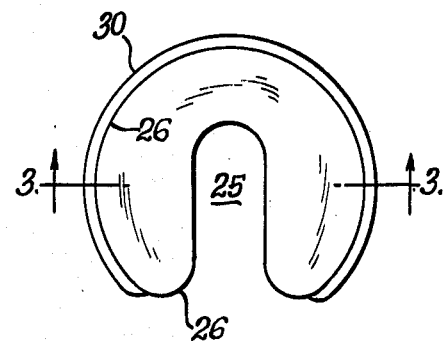
FIG. 2 is a top view of the tibial component of the prosthesis of FIG. 1.
Figure 3:
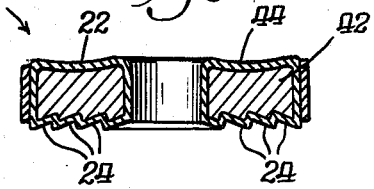
FIG. 3 is a side, sectional view of the tibial component of FIG. 4 taken though line 3—3.

Illustrated in FIGS. 2 and 3 are top and side sectional views of the pyrolytic carbon coated tibial component 14 further illustrating the metal stress band 30. In the embodiment of FIG. 2, the metal stress band 30 is not circumferentially continuous, but conforms to the radially outwardly directed portion of the perimeter surface 26. Because the metal stress bank 30 of the embodiment of FIG. 1 is not circumferentially continuous about the carbon coated substrate, it does not use its tensile strength to full advantage in order to control the tensile strain effects of compressive load against the top of the graphite substrate, and must rely more fully on its flexural modulus. Accordingly, the metal band of the embodiment of FIG. 1 will tend to be somewhat thicker than embodiments in which the band is circumferentially continuous.

Figure 4:
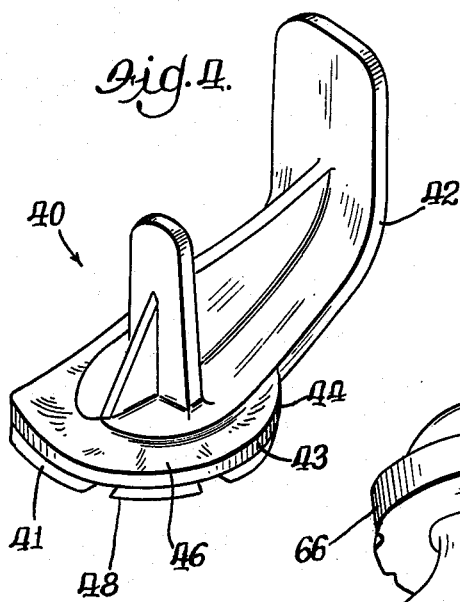
FIG. 4 is a perspective view of a unicompartmental knee joint prostheses illustrating an embodiment of the present invention.

In this connection, illustrated in FIG. 4 is a perspective view of a unicompartmental anatomic knee prosthesis 40 similarly comprising a femoral component 42 and a mating tibial component 44, which has a circumferentially continuous stress ring.

The tibial implant 44 has a generaly semicircular shape in the manner of conventional unicompartmental knee joint prostheses and comprises a biologically inert element 41 having a modulus of elasticity approximating that of natural bone, which as in the case of the embodiment of FIGS. 1–3, is fabricated from a suitably shaped, one-piece graphite substrate having a pyrolytic carbon coating. The carbon tibial element 44 has a highly polished concave mating surface 46 for interaction with the femoral implant component 42, and a bone joining face 48 which is provided with ridges and grooves for purposes of firm affixation to a suitably surgically prepared implant surface of the tibia. Surrounding the perimeter surface 41 of the carbon element and in conforming, compressional relationship therewith is a metal band 43 of chrome-cobalt alloy (for example, Vitallium) having a thickness of about 3/16 inch. The band is adjacent the upper joint surface 46, and provides reinforcement in respect of strains induced in the carbon element 41 by vertical loads. Tensile stresses resulting from application of vertical loads by the femoral component to the mating, highly polished concave upper surface 46 of the tibial component and transferred to the metal band 43 so that the carbon implant is reinforced against tensile fracture.

Figure 5:
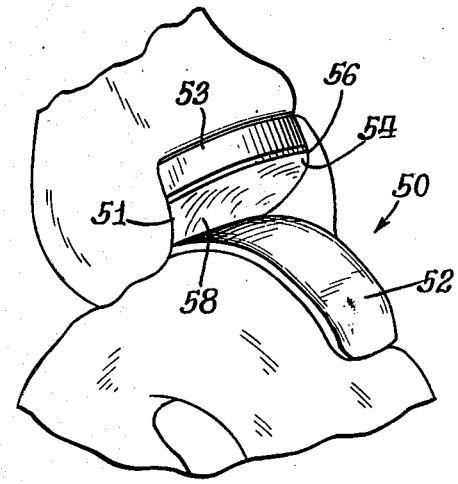
FIG. 5 is a perspective view of an artificial ankle prostheses illustrating an embodiment of the present invention.

While the previously described embodiments of the invention are knee joint prostheses, the invention also has applicability to other joint prostheses, and particularly those which are subjected to high compressive loads. In this connection, illustrated in FIG. 5 is an anatomically designed ankle joint prosthesis 50, of generally conventional shape which may be used for patients with ligament stability and intact medial, lateral, and posterior malleoli. The prostheses 50 comprises a talus component 52 and a distal tibial component 54 which are adapted to be implanted in a suitably surgically prepared ankle in accordance with conventional procedures.

The posterior aspect of the distal tibial component 54 is curved to approximate the natural contours of the joint, and has skirts on the medial and lateral aspect to prevent contact of the artificial talus component 52 against the medial or lateral malleolus.

The carbon distal tibial component 51, like the carbon proximal tibial component 21 of the knee joint prosthesis of FIG. 1, is formed of a polycrystalline graphite substrate material sold under the trade name POCO AXF graphite, which has a density of about 1.9 gm/cm, an average crystalline size of about 300 Angstroms, and an isotropy on the Bacon scale of nearly 1.0. The graphite has a Youngs modulus of elasticity of about $1.7 \times 10^6$ psi. The substrate is formed in the shape of the prosthesis and is coated with a layer of pyrolytic carbon about 500 microns thick having a density of about 1.9 gm/cm and a modulus of elasticity of $4 \times 10^6$ psi. The composite carbon element of the distal tibial component prosthesis has an effective modulus of elasticity which is in the range of that of natural living bone, which has a modulus of between about $2 \times 10^6$ psi and $4 \times 10^6$ psi. The distal tibial component 51 has a bone joining face adjacent the surgically prepared tibia, and has an arcuate, concave mating face 58 for rolling (and sliding) engagement with the arcuate talus element joint surface 52. The pyrolytic carbon coating of the tibial joint face is highly polished to provide a low friction, highly wear-resistant surface. As may be seen in the drawing of FIG. 5, the tibial component of the ankle prosthesis has a perimeter surface 56 which is intermediate and generally perpendicular to the bone joining face and the talus mating face 58.

Continuously surrounding the perimeter surface 52 of the carbon tibial component 51 and in compressional relationship therewith is a stainless steel band 53 having a thickness of about ⅛ inch and a modulus of elasticity of about $30 \times 10^6$ psi, which is about ten times that of the carbon tibial component 51. As shown in the drawing, the metal band 53 is positioned adjacent the curved talus-mating surface 58 of the carbon tibial joint element 51, and serves to reduce tensile stresses which are caused by vertical loads transmitted at the zone of contact between the tibial element 51 and the talus element 52.

Figure 6:
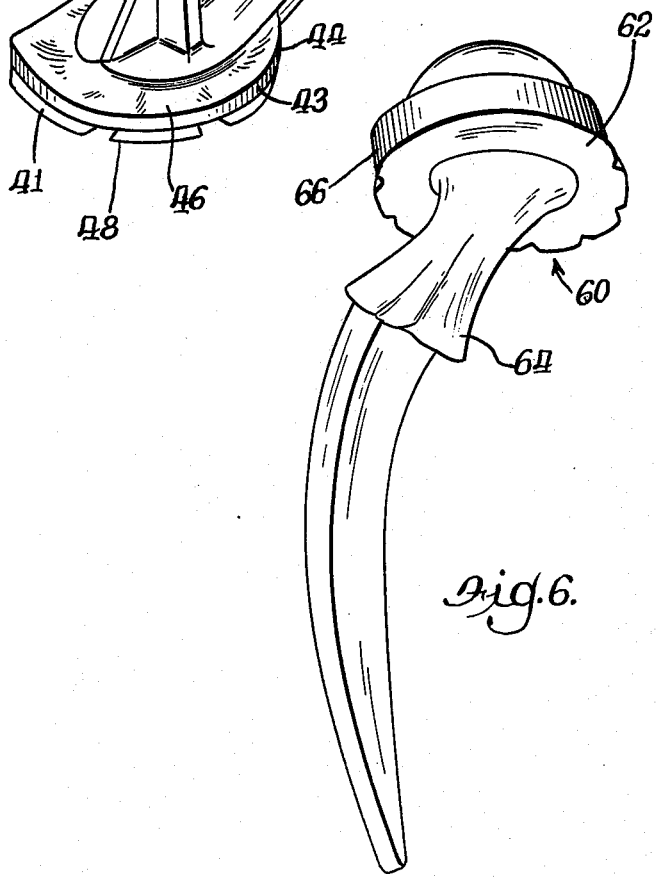
FIG. 6 is a perspective view of an artificial hip joint prostheses llustrating another embodiment of the present invention.

As indicated, prostheses embodying the present invention may be provided for various joints, and illustrated in FIG. 6 is an artificial hip joint 60, comprising an acetabular element cup 62 and a femoral ball element 64. The acetabular cup element is similar in shape to conventional polyethylene cup elements, and is fabricated from a suitable polycrystalline graphite substrate which is subsequently provided with a pyrolytic carbon coating. The structure of the carbon ball joint prosthesis element may include specific features of the carbon-hip joint prosthesis described in copending application Ser. No. 766,024, filed Feb. 7, 1977, now U.S. Pat. No. 4,126,924 and entitled "Socket and Joint Prostheses" [which is incorporated by reference herein]. In accordance with the present invention, the carbon coated acetabular element is also provided with a metallic chrome-cobalt alloy stress band 66 in a plane generally orthogonal to the loading axis of the acetabular cup with respect to its interaction with the femoral ball component. The stress band 66 continuously surrounds the exterior surface of the cup element adjacent the opening of the socket surface, and is in compressional press-fit-relationship with the carbon-coated substrate. The stress band effectively counteracts lateral tensile stresses in the carbon socket element in the plane orthogonal to the loading axis.

It will be appreciated that, through the present invention, improvements in carbon joint prostheses which are subjected to high compressive loads, has been provided. Although the invention has been described with respect to a number of specific embodiments, various modifications and adaptations will be apparent in view of the present disclosure. For example, metallic stress yokes or bands may be used in smaller joints such as finger joint elements described in my application Ser. No. 823,916 entitled "Ball and Socket Prosthetic Joint" executed on Aug. 12, 1977. Such modifications and adaptations are intended to be included within the scope of the following claims.

Various of the features of the invention are set forth in the following claims.

What is claimed is:

1. A stress-reinforced joint prosthesis element for prolonged or permanent reconstructive implantation in a living body comprising

- a dense isotropic graphite substrate of predetermined shape having a modulus of elasticity approximating the modulus of elasticity of natural bone, said substrate having a bone joining surface and an articulating joint surface adapted to receive substantial axial skeletal load forces tending to induce tensile strain in the joint prosthesis element transverse to the axial loading forces, and a perimeter surface adjacent said articulating joint surface.
- a dense adherent isotropic vapor-deposited pyrolytic carbon coating on said isotropic graphite substrate, said vapor-deposited pyrolytic carbon coating having increased strength when placed in compression and presenting a dense, smooth, low friction wear surface at said articulating joint surface, and a smooth exterior surface at said perimeter surface, and
- a metallic band in closely conforming compressional relationship against said smooth pyrolytic carbon coated perimeter surface adjacent said articulating joint surface with a compressive load from said band upon said perimeter surface which produces a strain at said perimeter surface not exceeding about 0.3% and having a modulus of elasticity at least about 5 times the modulus of elasticity of said carbon coated substrate, whereby said band functions to reduce said tensile strain induced upon application of said skeletal load forces, but said band being located intermediate said bone joining surface and said articulating wear surface such that said band does not carry any substantial portion of axial compressive load transmitted between said articulating wear surface and said bone joining surface upon application of said skeletal load forces.

2. A joint prosthesis element in accordance with claim 1 wherein said metallic band has a modulus of elasticity at least about 10 times the modulus of elasticity of said carbon coated substrate.

3. A joint prosthesis element in accordance with claim 2 wherein said prosthesis element is a unicompartmental tibial knee joint element having a perimeter surface between said bone joining face and said joint surface, and wherein said metal stress band is a circumferentially continuous band in compressional relationship with said perimeter surface.

4. A joint prosthesis element in accordance with claim 2 wherein said prosthesis element is a distal tibial ankle element.

5. A joint prosthesis element in accordance with claim 2 wherein said joint element is a hip socket element.